United States Patent [19]

Schmitz et al.

[11] 4,083,066

[45] Apr. 11, 1978

[54] HETEROLOGOUS ARTERIAL TRANSPLANTS

[75] Inventors: Heribert Schmitz, Trogen; Walter Stocklin, Ettingen, both of Switzerland

[73] Assignee: Solco Basel AG, Basel, Switzerland

[21] Appl. No.: 629,752

[22] Filed: Nov. 7, 1975

[30] Foreign Application Priority Data

Nov. 11, 1974 Germany .............................. 2453363

[51] Int. Cl.² .......................... A61F 1/24; A63B 51/02
[52] U.S. Cl. ......................................... 3/1.4; 8/94.11; 8/150.5; 128/334 R
[58] Field of Search .................... 128/334, 335.5, 1 R; 3/1, 1.4; 8/94.11, 150, 150.5

[56] References Cited

U.S. PATENT DOCUMENTS

| 1,628,966 | 5/1927 | Glasel ................................... 8/150.5 |
| 1,724,954 | 8/1929 | Merritt ............................. 8/150.5 X |
| 2,900,644 | 8/1959 | Rosenberg et al. ......................... 3/1 |
| 3,093,439 | 6/1963 | Bothwell ............................... 8/94.11 |
| 3,093,440 | 6/1963 | Bothwell ............................... 8/94.11 |
| 3,966,401 | 6/1976 | Hancock et al. ...................... 8/94.11 |

*Primary Examiner*—Dalton L. Truluck
*Attorney, Agent, or Firm*—Hammond & Littell

[57] ABSTRACT

In a process for the preparation of heterologous arterial transplants comprising freeing young animal arteries of surrounding tissue, ligating collateral branches, subjecting the resulting arteries to proteolysis to remove elastic fibers and muscle tissue to obtain collagen tubes and tanning the latter tubes to effect cross-linking, the improvement comprising effecting the proteoylsis and tanning steps in a continuous flow manner.

6 Claims, 1 Drawing Figure

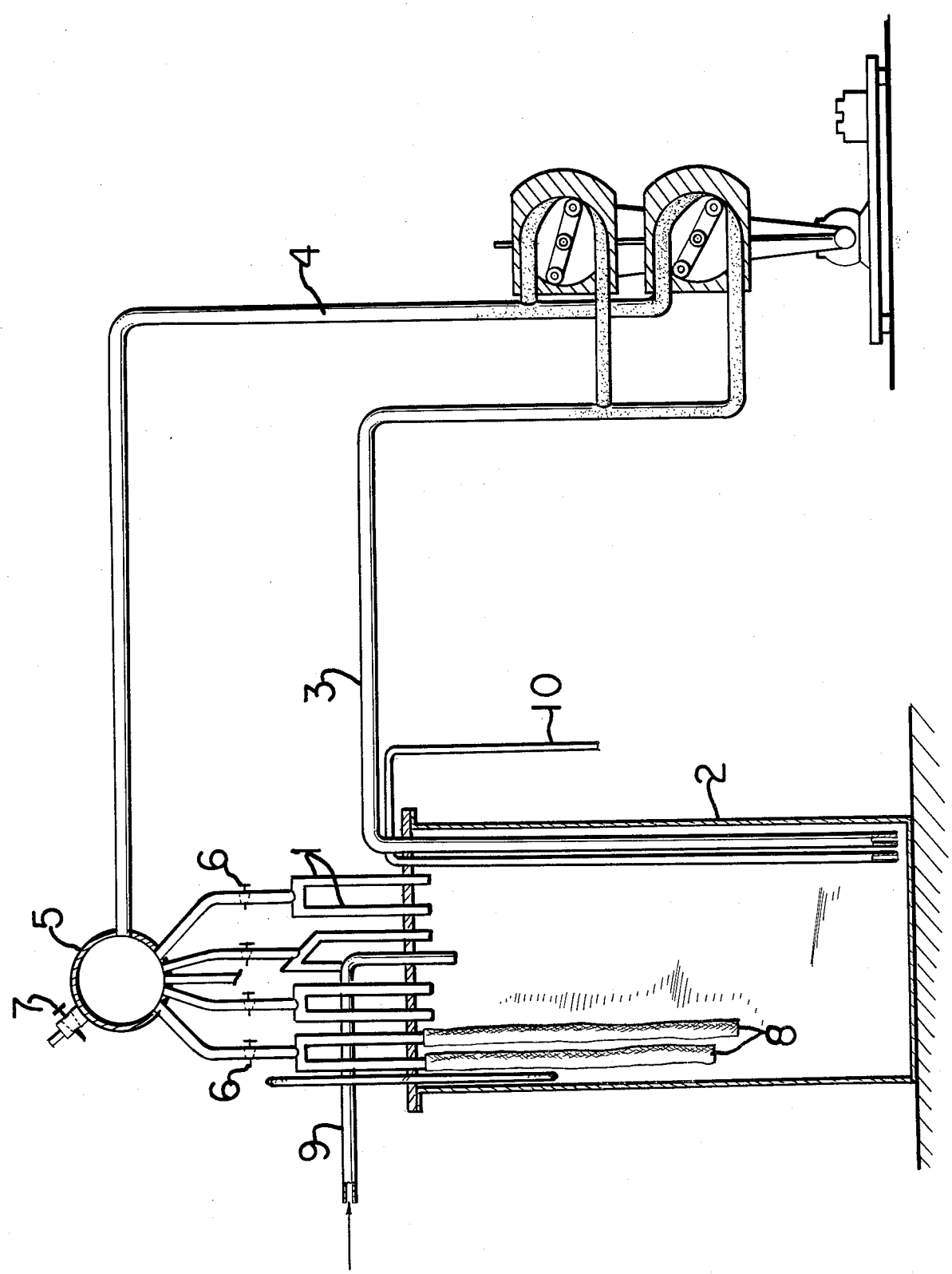

HETEROLOGOUS ARTERIAL TRANSPLANTS

STATE OF THE ART

There are presently three methods used for the replacement of defective arteries in humans, namely replacement with autologous veins, replacement with plastic implants and replacement with heterologous arterial transplants. While all three methods have been used with some success, none of the methods is completely satisfactory.

The great advantage of the replacement of a defective artery by an autologous vein is its immunological safety since the transplant is taken from the body of the patient. A disadvantage, however, is that the vein (e.g. vena saphena magna) must be obtained in an elaborate operation which requires multiple incisions and this represents an additional surgical risk for high-risk patients. Plastics prostheses are likewise immunologically safe and can in addition be kept in reserve. But they are not suitable for the risk-free bridging of joints.

Heterologous vascular transplants have proved very valuable on the basis of the properties that they are easy to suture and can be produced in practically any required length and the necessary diameter. By suturing together several pieces, it is easy to produce prosthetic pieces of any desired length. Since 2 to 3 skin cuts are sufficient for the transplantation of these heterologous vascular prostheses, the risk of an operation is low and they are, therefore, also suitable for higher-risk patients suffering, for example, from hypertonia, cardial insufficiency, diabetes mellitus etc.

Heterologous arterial transplants were obtained heretofore in the following manner. The arteries of suitable size, taken from the slaughter from mammals, e.g. calves and cattles, preferably the carotid arteries, are placed in a cold physiological saline and shipped from the slaughterhouse to the laboratory. There, the native vessels are liberated of the surrounding tissue, and the collateral branches are ligated with silk. But the preparation obtained this way is not transplantable, because the muscular tissue contained in the vessel, as well as the elastic fibers cause an antigen-antibody reaction (rejection reaction). For this reason, it is necessary to eliminate the antigenic tissue from the vessel and this is done by incubating the artery in an enzyme solution, e.g. a buffered ficin solution. Ficin is a proteolytic enzyme, that is protein splitting, obtained from fig tree sap. But other proteolytic enzymes, like trypsin and papain, can also be used. It is known that these proteolytic enzymes do not decompose the collagen-structure of the arteries.

The incubation of the arteries still containing muscular and elastic tissues in the ficin solution has the effect that these antigenic tissue portions are "digested" and this digestion process, like any enzymatic process, requires optimal pH standardization. After incubation in the enzyme or ficin solution, the proteolytically treated cattle or calf arteries are thoroughly washed with distilled water, and the enzymatic reaction is stopped for a definite period by introducing them into a sodium chlorite solution of a defined concentration.

The material remaining after this treatment consists of the collagen structure found in the artery per se. This collagen tube, though no longer antigenic, is not suitable for transplantation since it does not have the necessary tightness and stability. Tightness and stability are achieved by tanning the collagen tubes which are placed for a certain time in a buffered tanning solution. Suitable as tanning substances are dialdehyde starch, glyoxal and polyacrolein, but other tanning substances like formaldehyde, dialdehyde cellulose, glutaraldehyde etc. can also be used. This process is called "cross-linking." The imperviousness is checked by loading the vessel with compressed air up to a pressure of 240 mm Hg while the arteries are immerged in water.

The vascular prostheses obtained this way are mounted on glass rods with an adequate lumen and placed in sealable glass tubes which contain an appropriate solution for sterilization. The sterilization period is 14 days and can be achieved for example, in a preservative solution at 37° C in an incubator. The sterilized vascular prostheses remain in glass tubes until they are used.

This known procedure is a static method in that the proteolysis and the cross linkage steps are effected statically or a statical manner. Methods for the production of arterial transplants of the above indicated type are described, for example, in U.S. Pat. Nos. 2,900,644 and 3,093,439.

In the transplants produced this way, no special attention is given to the fact that the collagen, that is, the structural substance remaining after the decomposition, can result in certain immunological difficulties, particularly if not all the acutely or sub-acutely immunological material, particularly reticulin, has been removed in the conventional static treatment. The static treatment of the starting arteries also involves a certain risk of contamination with germs and a sometimes unnoticed infection of the arteries so that the immunological situation is unfavorably changed.

OBJECTS OF THE INVENTION

It is an object of the invention to provide an improved process for the preparation of heterologous arterial transplants from animal arteries.

It is a further object to provide the improved heterologous arterial transplants produced by the said process.

These and other objects and advantages of the invention will become obvious from the following detailed description.

THE INVENTION

The novel process of the invention for the preparation of heterologous arterial transplants comprises freeing young animal arteries of surrounding tissue, ligating collateral branches, subjecting the resulting arteries to proteoylsis to remove elastic fiber and muscle tissue to obtain collagen tubes and tanning the said tubes to effect cross-linking, the said proteoylsis and tanning steps being effected in a continuous flow manner.

The animals whose arteries used are the same as those used in known processes and are the usual slaughter animals with the exception that the animals used are as young as possible. Examples of suitable animals are calves, sheep, pigs, etc. preferably less than 3 months old.

The conducting of the proteoylsis and tanning or cross-linking steps in a continuous flow or dynamic manner avoids the disadvantages of the known interrupted process and ensures that the arteries are traversed by the respective treating solutions. The method ensures complete treatment of the arteries, particularly the inner lumen.

The method of the invention permits the connection of the arteries with coupling pieces such as glass tubes so any number of pieces can be connected at the same time to ensure complete identity of the final product. Another advantage is that the successive steps of digestion, washing, stopping the digestion, washing, cross-linking and washing may be carried out continuously in a suitable apparatus. The method results in a prosthesis which is essentially immunologically safe and highly suitable as a replacement for defective arteries.

The following examples illustrate the invention. However, it should be understood that the invention is not intended to be limited to the specific embodiments.

EXAMPLE 1

Carotid arteries of calves were collected and were shipped in an ice-cooled, 0.9% physiological salt solution to a laboratory where they were freed of any surrounding tissue and any collateral branches were sewn closed with silk thread (unsterile 000). The resulting arteries were used as is in example 3.

EXAMPLE 2

16.2 g of corn starch (based on the dry weight) were stirred into 100 ml of distilled water and a solution of 23.5 g of sodium metaperiodate in 300 ml of distilled water was added dropwise with stirring over one hour to the resulting suspension. The mixture was stirred for another 18 hours at 25° C and was then vacuum filtered. The residue on the filter was washed 6 times with 50 ml portions of distilled water and the last rinse was free of iodate in a test with potassium iodide-starch paper. The residue was washed with 100 ml of acetone to avoid the formation of a horny product and was then dried at 40° C under vacuum for 24 hours to obtain 17.2 g (15.7 g based on dry weight) of dialdehyde starch.

EXAMPLE 3

This example illustrates the treatment of the arteries using the process of the invention in the apparatus illustrated in FIG. 1. 20 arteries treated in Example 1 were attached to tubes 1 and suspended in container 2. A ficin solution consisting of 7.5 liters of deionized water preheated to 30° C, 75 g of ficin and 7.5 g of L-(+)-cystein were prepared in a 10 liter beaker and the resulting solution was placed in container 2. The ficin solution was standardized with 1N sodium citrate solution with a pH of 6.0 and the container 2 was placed in a water bath of 45°-50° C. Then, petcocks 6 were closed and the ficin solution in container 2 was removed by tube 3 and pumped by feed line 4 into distribution bell 5. When the bell 5 was filled with ficin solution, petcock 7 was closed and petcocks 6 were opened whereby the ficin solution passed through lines 1 and through the arteries 8 to container 2. The solution was circulated for 3 hours in this manner at a constant internal temperature of 38° C.

After this time, the ficin solution was drained off and the water bath was removed. Deionized water was then introduced into container 2 by feed line 9 and the ficin treated arteries were washed several times with deionized water. The rinse water was then removed by line 10 and a solution of 93.7 g of sodium chlorite (80%) in 7.5 liters of deionized water was added to container 2 and circulated through the apparatus in the same fashion as the ficin solution for 18 hours at room temperature. Then, the sodium chlorite solution was removed by line 9 and the arteries were again rinsed with deionized water introduced by feed line 9.

A solution of 97.5 g of the dialdehyde starch of Example 1 in 7.5 liters of deionized water was buffered to a pH of 8.8 with a sodium bicarbonate solution and was then added to container 2 by feed line 9. The said solution was then circulated through the apparatus as before for 24 hours at room temperature and was then removed by line 10. The apparatus was the rinsed several times with deionized water introduced through feed line 9.

The resulting arteries were then tested for leaks at an internal pressure of 240 Torr using the pump of a sphygmomanometer and a water bath. Any leaking areas were then sewed shut with silk thread. The satisfactory arteries were mounted on glass rods and placed in a glass tube sealed at one end and filled with a 50-50 (by volume) solution of ethanol and distilled water containing 1% of propylene oxide. The tube was then sealed with a rubber stopper and insulating tape and was placed in an incubator at 37° C for 14 days.

EXAMPLE 4

Arteries were treated as in Example 3 but the ficin solution was replaced by a 2% trypsin solution standarized with a phosphate-citrate buffer solution to a pH of 7.8.

EXAMPLE 5

Using the procedure of Example 3, arteries were treated with a 0.5% glyoxal solution buffered with a 10% sodium bicarbonate solution to a pH of 8.8 in place of the 1.3% dialdehyde solution.

Various modifications of the products and process of the invention may be made without departing from the spirit or scope thereof and it should be understood that the invention is to be limited only as defined in the appended claims.

We claim:

1. A process for the preparation of heterologous arterial transplants comprising freeing animal arteries of surrounding tissue, ligating collateral branches, subjecting the resulting arteries to proteolysis to remove elastic fiber and muscle tissue to obtain collagen tubes and tanning said tubes to effect cross-linking, the said proteolysis and tanning steps being effected by proteolytic and tanning solutions which continuously flow in one direction both through said arteries and along the outer surface of said arteries.

2. The method of claim 1 wherein the arteries are from young animals.

3. The method of claim 1 wherein the arteries are from newborn animals.

4. The method of claims 1 wherein the arteries are a plurality of arteries connected together.

5. The method of claim 1 wherein the arteries are calf arteries.

6. The arterial transplants produced by the process of claim 1.

* * * * *